United States Patent
Bonduelle et al.

(10) Patent No.: US 10,322,984 B2
(45) Date of Patent: *Jun. 18, 2019

(54) OLEFIN METATHESIS METHOD USING A CATALYST CONTAINING ALUMINIUM AND MOLYBDENUM INCORPORATED BY MEANS OF AT LEAST TWO PRECURSORS

(71) Applicant: IFP Energies nouvelles, Rueil-Malmaison (FR)

(72) Inventors: Audrey Bonduelle, Francheville (FR); Alexandra Chaumonnot, Lyons (FR); Damien Delcroix, St Maurice L'Exil (FR); Christophe Vallee, St Genis Laval (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/749,368

(22) PCT Filed: Jul. 26, 2016

(86) PCT No.: PCT/EP2016/067829
§ 371 (c)(1),
(2) Date: Jan. 31, 2018

(87) PCT Pub. No.: WO2017/021232
PCT Pub. Date: Feb. 9, 2017

(65) Prior Publication Data
US 2018/0230071 A1    Aug. 16, 2018

(30) Foreign Application Priority Data
Jul. 31, 2015    (FR) ..................... 15 57367

(51) Int. Cl.
*C07C 6/04* (2006.01)
*B01J 23/28* (2006.01)
(Continued)

(52) U.S. Cl.
CPC ................. *C07C 6/04* (2013.01); *B01J 21/02* (2013.01); *B01J 23/002* (2013.01); *B01J 23/28* (2013.01);
(Continued)

(58) Field of Classification Search
None
See application file for complete search history.

(56) References Cited

U.S. PATENT DOCUMENTS

| | | | |
|---|---|---|---|
| 2003/0023125 A1* | 1/2003 | Euzen | B01J 23/28 585/646 |
| 2014/0179973 A1 | 6/2014 | Debecker | |

FOREIGN PATENT DOCUMENTS

| | | |
|---|---|---|
| CN | 101254470 A | 9/2008 |
| CN | 104056651 A | 9/2014 |

(Continued)

OTHER PUBLICATIONS

Carrier, "Ligand-promoted alumina dissolution in the preparation of MoOx/Al2O3 catalysts: evidence for the formation and deposition of an Anderson-type alumino heteropolymolybdate", Journal of the American Chemical Society, American Chemical Society, US, vol. 119, Jan. 1, 1997 (Year: 1997).*

(Continued)

*Primary Examiner* — Philip Y Louie
(74) *Attorney, Agent, or Firm* — Millen, White, Zelano and Branigan, P.C.

(57) ABSTRACT

The invention relates to a process for the metathesis of olefins implemented with a catalyst comprising a mesoporous matrix and at least the elements molybdenum and (Continued)

aluminum, said elements being incorporated into said matrix by means of at least two precursors of which at least one precursor contains molybdenum and at least one precursor contains aluminum.

18 Claims, 1 Drawing Sheet

(51) Int. Cl.

| | | |
|---|---|---|
| *B01J 27/19* | (2006.01) | |
| *B01J 35/10* | (2006.01) | |
| *B01J 37/08* | (2006.01) | |
| *B01J 37/02* | (2006.01) | |
| *B01J 23/00* | (2006.01) | |
| *B01J 23/882* | (2006.01) | |
| *B01J 37/00* | (2006.01) | |
| *B01J 21/02* | (2006.01) | |
| *C07C 11/04* | (2006.01) | |
| *C07C 11/06* | (2006.01) | |
| *C07C 11/08* | (2006.01) | |

(52) U.S. Cl.
CPC .............. *B01J 23/882* (2013.01); *B01J 27/19* (2013.01); *B01J 35/1019* (2013.01); *B01J 35/1042* (2013.01); *B01J 35/1061* (2013.01); *B01J 37/0018* (2013.01); *B01J 37/0205* (2013.01); *B01J 37/0236* (2013.01); *B01J 37/088* (2013.01); *B01J 2523/00* (2013.01); *B01J 2523/31* (2013.01); *B01J 2523/51* (2013.01); *B01J 2523/68* (2013.01); *B01J 2523/845* (2013.01); *C07C 11/04* (2013.01); *C07C 11/06* (2013.01); *C07C 11/08* (2013.01); *C07C 2521/02* (2013.01); *C07C 2521/08* (2013.01); *C07C 2523/28* (2013.01); *Y02P 20/52* (2015.11)

(56) References Cited

FOREIGN PATENT DOCUMENTS

| FR | 2977890 A1 | 1/2013 |
| FR | 3007029 A1 | 12/2014 |

OTHER PUBLICATIONS

International Search Report PCT/EP2016/067829 dated Nov. 23, 2016.

Radu Dorin Andrei et al: "Ethylene to Propylene by One-Pot Catalytic Cascade Reactions", ACS Catalysis, vol. 5, No. 5, May 1, 2015 (May 1, 2015), US, pp. 2774-2777, XP055273374, ISSN: 2155-5435.

Dazhou Zhang et al: "Metathesis of 1-Butene to Propene over Mo/Ai 2 O 3 @SBA-15: Influence of Alumina Introduction Methods on Catalytic Performance", Chemistry—An Asian Journal, vol. 10, No. 8, Jun. 25, 2015 (Jun. 25, 2015), DE, pp. 1647-1659, XP055273369, ISSN: 1861-4728.

* cited by examiner

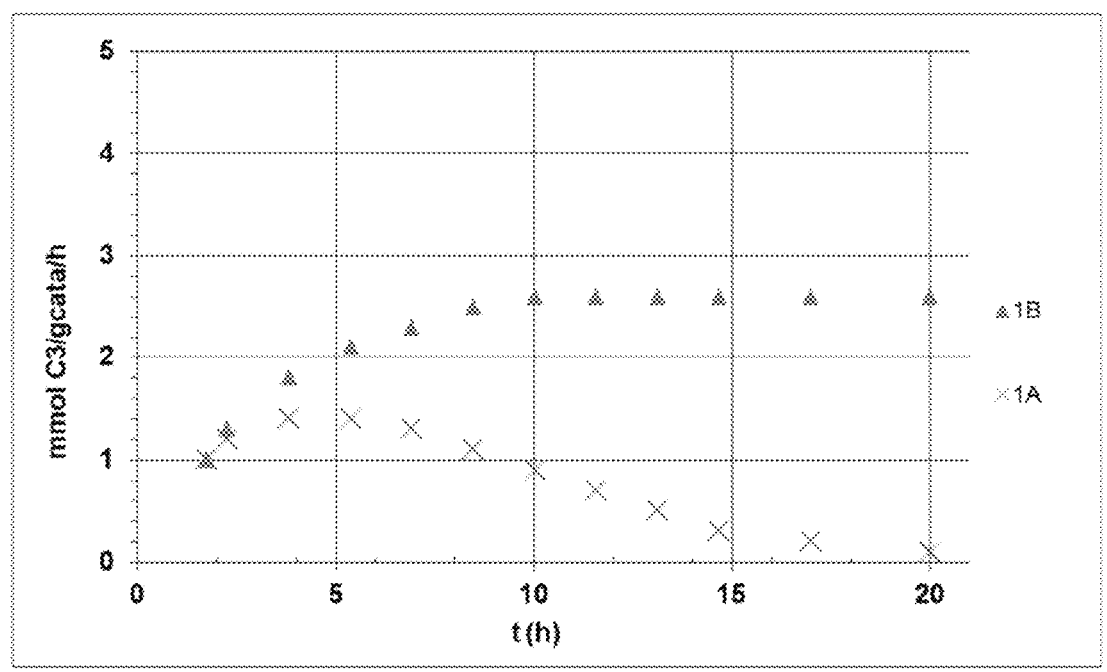

OLEFIN METATHESIS METHOD USING A CATALYST CONTAINING ALUMINIUM AND MOLYBDENUM INCORPORATED BY MEANS OF AT LEAST TWO PRECURSORS

The present invention relates to a process for the metathesis of olefins using a catalyst prepared from at least two precursors of which at least one precursor contains molybdenum and at least one precursor contains aluminium.

PRIOR ART

The metathesis of olefins is an important reaction in various fields of chemistry. In organic synthesis, this reaction, catalyzed by organometallic complexes, is used in order to obtain various high added value molecules. In petrochemistry, the metathesis of olefins is of great practical interest in particular for the rebalancing of light olefins originating from steam cracking, such as ethylene, propylene and butenes. In particular, the cross-metathesis of ethylene with 2-butene in order to produce propylene is a reaction of interest given the increasing use of propylene in the market.

Different types of catalysts are capable of being used in the metathesis reaction. It is possible to use homogeneous catalysts, the constituent elements of which are all soluble in the reaction medium, or heterogeneous catalysts which are insoluble in the reaction medium.

The metathesis of light olefins utilizes heterogeneous catalysts. A known solution is the technology described in U.S. Pat. No. 8,586,813, which uses a catalyst based on tungsten oxide deposited on a silica support $WO_3/SiO_2$. However, the heterogeneous catalysts based on tungsten operate at a relatively high temperature, generally at a temperature greater than 300° C. and are only moderately active.

Moreover, it is known that metathesis catalysts based on rhenium oxide $Re_2O_7$ such as those described in the publication by Chauvin et al. Journal of Molecular Catalysis 1991, 65, 39 have good activities at temperatures close to ambient temperature. Other catalysts based on molybdenum oxide such as those described in the publication D. P. Debecker et al., J. Catal., 2011, 277, 2, 154 and patents GB 1,164,687 and GB 1,117,968 owned by the company Shell have been also developed. Shell's process uses, for example, catalysts based on molybdenum and cobalt oxides deposited on an aluminium support $CoMoO_4/Al_2O_3$ and doped with phosphorus, as described in U.S. Pat. No. 4,754,099.

One benefit of molybdenum (Mo) is that it is less expensive than rhenium (Re). In addition, its stability and its activity are intermediate between those of rhenium (Re) and tungsten (W). In particular, molybdenum can be active starting from ambient temperature.

The preparation of catalysts based on molybdenum oxides ($MoO_3$) is carried out in a standard fashion by impregnation with an aqueous solution of a molybdenum salt or a heteropolyanion containing molybdenum such as for example the isopolyanion ammonium heptamolybdate on a support such as silica, alumina or a porous aluminosilicate. The catalysts prepared from precursors of the ammonium heptamolybdate type however lack activity and stability. Catalysts based on other heteropolyanions such as $H_3PMo_{12}O_{40}$ have been prepared and make it possible to appreciably increase activity, but need further improvement.

Therefore there is still a need to develop new catalysts having improved performances in terms of activity and selectivity for the metathesis reaction of olefins and more particularly for the metathesis between ethylene and 2-butene for the production of propylene.

The Applicant, in his research to improve the performances of the heterogeneous catalysts for the metathesis of olefins, has developed new catalysts for the metathesis reaction of olefins. These catalysts are prepared from a mesoporous matrix and at least two precursors of which at least one precursor contains molybdenum and at least one precursor contains aluminium. Unexpectedly, it has been found that the use of these types of precursors for the preparation of the catalyst according to the invention improved the activity and the stability of the heterogeneous catalyst obtained for the metathesis reaction of olefins, compared with the catalysts prepared using other precursors of the prior art. The conversion of the olefins is thereby improved. The stability of the catalyst is also improved.

An objective of the present invention is to provide a process for the metathesis of olefins using a catalyst having improved performances in terms of activity and selectivity compared with the use of heterogeneous catalysts of the prior art.

The catalysts according to the invention have the advantage of being able to operate over longer time cycles before regeneration, which has a significant economic impact on the operating costs of the process according to the invention.

SUBJECT OF THE INVENTION

The present invention relates to a process for the metathesis of olefins carried out by bringing the olefins into contact with a catalyst comprising a mesoporous matrix and at least the elements molybdenum and aluminium, said elements being incorporated into said matrix by means of at least two precursors of which at least one precursor contains molybdenum and at least one precursor contains aluminium.

Molybdenum-Containing Precursor

Advantageously, the molybdenum-containing precursor according to the present invention is a precursor of the coordination complex type based on molybdenum and/or of the polyoxometallate type based on molybdenum and/or of the (thio)molybdate type.

When the molybdenum-containing precursor according to the present invention is a precursor of the coordination complex type based on molybdenum, it advantageously corresponds to formula (I)

$$Mo_m(=Y)_n(\equiv N)_{n'}(X)_o(=CR_2)_r \qquad (I)$$

in which, the Y groups, identical to or different from each other, can be selected from O, S and NR', the X groups, identical to or different from each other, can be selected from the halides, such as F, Cl, Br, I, chlorate, bromate, iodate, nitrate, sulphate or hydrogen sulphate, alkylsulphate, thiosulphate, carbonate or hydrogen carbonate, phosphate or hydrogen phosphate or dihydrogen phosphate, the substituted or unsubstituted alkyl, cycloalkyl or aryl, substituted or unsubstituted cyclopentadienyl groups, the alkoxy, aryloxy, siloxy, amide, hydrido, nitro, carboxylate, acetylacetonate, sulphonate, β-diketiminate, iminopyrrolide, amidinate, borate, cyanide, cyanate, thiocyanate or $NR_2$—$CS_2^-$ groups, the R and R' groups, identical to or different from each other, can be selected from the alkyl and aryl groups, preferably comprising between 1 and 10 carbon atoms, the alkoxy and aryloxy groups, m is equal to 1 or 2, n is comprised between 0 and 4,
n' is comprised between 0 and 2,
o is comprised between 0 and 10,
r is comprised between 0 and 2,
n+n'+o+r is greater than or equal to 1, preferably greater than or equal to 2.

According to the invention, the precursor of the coordination complex type based on molybdenum can also contain in its coordination sphere one or more L-type ligands, optionally polydentate. The L-type ligand can be selected from the carbon-containing compounds, such as carbon monoxide, the alkenes, alkynes, the phosphorus-containing compounds such as the phosphines, phosphinites, phosphonites, phosphites, the oxygen-containing compounds such as water, the ethers, the nitrogen-containing compounds such as the amines, the nitrogen-containing aromatic compounds such as pyridine and/or phenantroline, and/or the sulphur-containing compounds such as the thioethers.

The precursor of the coordination complex type based on molybdenum corresponding to formula (I) is incorporated by its chemical nature in the neutral form.

The precursor of the coordination complex type based on molybdenum can for example be selected from the following compounds: $MoCl_5$, $MoOCl_4$, $MoSCl_4$, $Mo(C_5H_5)Cl_4$, $Mo(SO_4)_3$, $Mo_2(C_5H_5)_2(CO)_6$, $Mo(\!=\!CH\!-\!C(Me)_2Ph)(\!=\!N\text{-}Ph(^iPr)_2)(OSO_2CF_3)_2(CH_3O(CH_2)_2OCH_3)$, $MoO_2$(acetylacetonate)$_2$, $Mo(\!=\!O)(OSi^tBu_3)_4$, $Mo(\equiv\!N)(OSiPh_3)_3(C_6H_6N)$, $Mo[OOCCH(C_2H_5)C_4H_9]_4$, $Mo[OOCC_7H_{15}]_2$, molybdenum naphthenate, $Mo(CO)_6$, etc.

When the molybdenum-containing precursor according to the present invention is a precursor of the polyoxometallate type based on molybdenum, it advantageously corresponds to formula (II)

$$(X_xMo_mM_bO_yH_h)^{q-}.nH_2O \qquad (II)$$

in which,
x is greater than or equal to 0,
m is greater than or equal to 2,
b is greater than or equal to 0,
y is greater than or equal to 7,
h is comprised between 0 and 12,
q is comprised between 1 and 20,
n is comprised between 0 and 200,
x, m, b, y, h, n and q being integers, X being an element selected from phosphorus, silicon and boron, M being a metallic element selected from aluminium, zinc, nickel, cobalt, tungsten, vanadium, niobium, tantalum, iron and copper, preferably M is a metallic element selected from aluminium, cobalt and tungsten, more preferably from aluminium and cobalt and yet more preferably, the metallic element M is cobalt.

The precursor of the polyoxometallate type based on molybdenum corresponding to formula (II) can be incorporated into the mesoporous matrix in the form of a salt or in the form of an acid. In the case where the precursor of the polyoxometallate type based on molybdenum corresponding to formula (II) is incorporated in the form of an acid, the charge $q^-$ is compensated for by protons $H^+$. When the precursor of the polyoxometallate type based on molybdenum corresponding to formula (II) is introduced in the form of salt, the counter-ions of the salt of the polyoxometallate are selected from all the cations known to a person skilled in the art. By way of example the proton, the ammoniums, phosphoniums, alkalis, alkaline-earths, transition elements, etc. can be mentioned. The polyoxometallate salt based on molybdenum can comprise a mixture of one and the same cation or different cations.

The precursor of the polyoxometallate type is preferentially selected from the isopolyanions based on molybdenum and the heteropolyanions based on molybdenum.

The isopolyanion precursors based on molybdenum according to the invention, correspond to the precursor according to formula (II)

$$(X_xMo_mM_bO_yH_h)^{q-}.nH_2O \qquad (II)$$

in which the subscript x of the element X is equal to 0, all other things being equal with respect to the definition of the subscripts and elements according to the invention. The precursors of the isopolyanion type based on molybdenum according to the invention can be selected for example from $Mo_2O_7^-$, $Mo_7O_{24}^{6-}$.

The precursor of the polyoxometallate type is preferentially selected from the isopolyanions and heteropolyanions. When isopolyanions are used, the element X shown in formula (II) above is absent and x=0. The precursors of the isopolyanion type can be selected from $Mo_2O_7^-$, $Mo_7O_{24}^{6-}$.

The precursor of the polyoxometallate type based on molybdenum according to the invention can contain one or more metallic elements M selected from aluminium, zinc, nickel, cobalt, tungsten, vanadium, niobium, tantalum, iron and copper, in substitution for one or more molybdenum atoms contained in said polyoxometallate precursor of formulae described above. Preferably, the metallic element M is selected from aluminium, cobalt and tungsten, more preferably from aluminium and cobalt and yet more preferably, the metallic element M is cobalt.

When the precursor of the polyoxometallate type used in the preparation of the catalyst utilized in the metathesis process according to the invention does not contain a metallic element M other than molybdenum, it is advantageously selected from the group formed by a Strandberg heteropolyanion of formula $X_2Mo_5O_{23}H_h^{q-}.nH_2O$, an Anderson heteropolyanion of formula $XMo_6O_{24}H_h^{q-}.nH_2O$, the Keggin heteropolyanion of formula $XMo_{12}O_{40}H_h^{q-}.nH_2O$, a lacunary Keggin heteropolyanion of formula $XMo_{11}O_{39}H_h^{q-}.nH_2O$, a lacunary Keggin heteropolyanion of formula $XMo_9O_{34}H_h^{q-}.nH_2O$, a Dawson heteropolyanion of formula $X_2Mo_{18}O_{62}H_h^{q-}.nH_2O$, a Preyssler heteropolyanion of formula $X_5Mo_{30}O_{110}H_h^{q-}.nH_2O$ with X, h and q having the above-mentioned definitions according to the invention.

When the precursor of the polyoxometallate type based on molybdenum used in the preparation of the catalyst utilized in the metathesis process according to the invention contains a metallic element M other than molybdenum, M preferably being cobalt, it is advantageously selected from the group formed by a Strandberg heteropolyanion of formula $X_2Mo_4CoO_{23}H_h^{q-}.nH_2O$, an Anderson heteropolyanion of formula $XMo_5CoO_{24}H_h^{q-}.nH_2O$, a Keggin heteropolyanion of formula $XMo_{11}CoO_{40}H_h^{q-}.nH_2O$, a lacunary Keggin heteropolyanion of formula $XMo_{10}CoO_{39}H_h^{q-}.nH_2O$, a lacunary Keggin heteropolyanion of formula $XMo_8CoO_{34}H_h^{q-}.nH_2O$, a Dawson heteropolyanion of formula $X_2Mo_{17}CoO_{62}H_h^{q-}.nH_2O$, a Preyssler heteropolyanion of formula $X_5Mo_{29}CoO_{110}H_h^{q-}.nH_2O$ with X, h and q having the above-mentioned definitions according to the invention, the preparation of which is precisely described in application FR 2,764,211.

When the molybdenum-containing precursor according to the present invention is a precursor of the (thio)molybdate type, it advantageously corresponds to formula (III)

$$C_c(MoY_4)_z \qquad (III)$$

in which
- C represents an organic or inorganic cation, selected from all the cations known to a person skilled in the art. By way of example the following can be mentioned protons, ammoniums, phosphoniums, alkalis, alkaline-earths, transition elements,
- the Y groups, identical to or different from each other, can be selected from O and S,
- c is comprised between 1 and 4,
- z is comprised between 1 and 10.

The precursor of the (thio)molybdate type containing molybdenum can for example be selected from the following compounds: $(NH_4)_2MoS_4$, $(NEt_4)_2MoS_4$, $Na_2MoO_4$, $(NH_4)_2MoO_4$, $Fe_2(MoO_4)_3$.

One or more precursors of the type corresponding to formula (I), (II) and/or (III) can be used in the process according to the invention.

Aluminium-Containing Precursor

Advantageously, the aluminium-containing precursor according to the present invention is a precursor selected from any source of aluminium and advantageously selected from the precursors of the coordination complex type based on aluminium and/or the precursors of the aluminium salt type and/or the precursors of the heteropolyanion salt type based on aluminium and/or any colloidal solution of alumina.

When the precursor based on aluminium according to the present invention is a precursor of the coordination complex type based on aluminium, it advantageously corresponds to formula (IV)

$$Al_nR_m \cdot xH_2O \qquad (IV)$$

in which,
- n is comprised between 1 and 3,
- m is comprised between 1 and 3,
- x is comprised between 0 and 200,
- the R groups identical to or different from each other, can be selected from hydrogen, the halides, such as F, Cl, Br, I, chlorate, bromate, iodate, nitrate, sulphate or hydrogen sulphate, alkylsulphate, thiosulphate, carbonate or hydrogen carbonate, phosphate or hydrogen phosphate or dihydrogen phosphate, the substituted or unsubstituted alkyl, alkenyl, alkynyl, cycloalkyl or aryl, substituted or unsubstituted cyclopentadienyl groups, the hydroxy, alkoxy, aryloxy, carboxylate, nitrate, acetylacetonate, sulphonate, perchlorate groups.

According to the invention, the precursor of the coordination complex type based on aluminium can also contain in its coordination sphere one or more L-type ligands, optionally polydentate. The L-type ligand can be selected from the carbon-containing compounds, such as carbon monoxide, the alkenes, the alkynes, phosphorus-containing compounds such as the phosphines, phosphinites, phosphonites, phosphites, the oxygen-containing compounds such as water, the ethers, the nitrogen-containing compounds such as the amines, the nitrogen-containing aromatic compounds such as pyridine and/or phenantroline, the salen and salan ligands of the cyclohexane-diamino-N,N'-bis(alkyl)salicylidene type and/or the sulphur-containing compounds such as the thioethers.

The precursor of the coordination complex type based on aluminium corresponding to formula (IV) is, by its chemical nature, incorporated in neutral form.

The precursor of the coordination complex type based on aluminium can for example be selected from the following compounds: $AlCl_3$, $Al(ClO_4)_3 \cdot 9H_2O$, $Al(acetylacetonate)_3$, $Al(CF_3COCHCOCF_3)_3$, $Al[OCH(CH_3)_2]_3$, $Al_2(SO_4)_3 \cdot 18H_2O$, $Al[OOCCH(C_2H_5)C_4H_9]_2$, $(C_2H_5)_2AlCl$, $Al(CH_3)_3$.

When the aluminium-containing precursor according to the present invention is a precursor of the aluminium salt type, it advantageously corresponds to formula (V)

$$[Al_nR_m]^-[C]^+ \cdot nH_2O \qquad (V)$$

in which,
- n is comprised between 1 and 3,
- m is comprised between 1 and 3,
- x is comprised between 0 and 200,
- the R groups identical to or different from each other, can be selected from hydrogen, the oxo group, the halides such as F, Cl, Br, I, the substituted or unsubstituted alkyl, alkenyl, alkynyl, cycloalkyl or aryl, substituted or unsubstituted cyclopentadienyl groups, the hydroxy, alkoxy, aryloxy, carboxylate, sulphonate, nitrate, acetylacetonate, perchlorate groups,
- C is selected from hydrogen, the alkali, alkaline-earth elements, transition metals, post-transition metals and rare earths, the ammonium and phosphonium cations.

The precursor of the aluminium salt type containing aluminium can for example be selected from the following compounds: $[AlO_2]^-[Na]^+$, $[AlCl_4]^-[Cs]^+$, $[Al(SO_4)_2]^-[NH_4]^+$, $[AlH_4]^-[Li]^+$, etc.

When the aluminium-containing precursor according to the present invention is a precursor of the heteropolyanion salt type based on aluminium, it advantageously corresponds to formula (VI)

$$(Al_aM1_mM2_bX_xO_yH_h)^{q-}(C^{r+})_c \cdot nH_2O \qquad (VI)$$

in which,
- a is greater than or equal to 0,
- m is greater than or equal to 1,
- b is greater than or equal to 0,
- x is greater than or equal to 0,
- y is greater than or equal to 10,
- h is comprised between 0 and 12,
- q is comprised between 0 and 20,
- r is comprised between 0 and 20,
- c is comprised between 0 and 20,
- n is comprised between 0 and 200,
- x, m, y, h, n and q being integers, X being an element selected from phosphorus, silicon and boron, M1 and M2, identical to or different from each other, being metallic elements selected from aluminium, zinc, nickel, cobalt, molybdenum, tungsten, vanadium, niobium, tantalum, iron and copper,
- C represents one or more atoms, identical or different, hydrated or non-hydrated, selected from the elements of the periodic table capable of existing in the cationic form, such as hydrogen, the alkali, alkaline-earth elements, transition metals, post-transition metals and rare earths, in hydrated or non-hydrated forms, selected from the oxygen-containing and/or nitrogen-containing and/or phosphorus-containing organic cations, such as the ammonium and phosphonium cations.

According to the invention, the precursor of the heteropolyanion salt type based on aluminium can be stabilized by one or more additional organic species selected from oxygen-containing and/or nitrogen-containing organic molecules, such as histidine, piperazine, choline, urea, the copper complexes of phenantroline, acetate ion, acetic acid, used alone or in a mixture.

The precursor of the heteropolyanion salt type based on aluminium can for example be selected from the following compounds: $[Al(OH)_6Mo_6O_{18}]^{3-}[(C_6H_{10}N_3O_2)_2Na(H_2O)_2]^{3+}.6H_2O(C_6H_{10}N_3O_2=$histidinium$)$, $[Al(OH)_6Mo_6O_{18}]^{3-}\{Na[Me_3N(CH_2)_2OH]_2\}^{3+}.4NH_2CONH_2.2H_2O$, $[Al(OH)_6Mo_6O_{18}]^{3-}.(H_3O^+)[Cu(C_6NO_2H_4)($phenantroline$)(H_2O)]^+{}_2.5H_2O$, $[Al(OH)_6Mo_6O_{18}]^{3-}[Al(H_2O)_6]^{3+}.10H_2O$, $[Al(OH)_6Mo_6O_{18}]^{3-}[(NH_4)^+]_3.7H_2O$.

One or more precursors of the coordination complex type, corresponding to formulae (IV), (V) and/or (VI) can be used.

The mesoporous matrix according to the invention is advantageously a matrix based on the oxide of at least one element X selected from silicon, aluminium, titanium, zirconium, magnesium, lanthanum, cerium and mixtures thereof. Preferably, the mesoporous matrix according to the invention is advantageously a matrix based on the oxide of at least one element X selected from silicon, titanium, zirconium, magnesium, lanthanum, cerium and mixtures thereof. Preferably, the element X is silicon or a mixture of aluminium and silicon. More preferably, the element X is silicon.

Said matrix based on oxide described as mesoporous is understood to mean according to the present invention a matrix comprising pores the size of which varies between 2 and 50 nm according to the IUPAC classification (K. S. W. Sing, D. H. Everett, W. R. A. Haul, L. Moscou, J. Pierotti, J. Rouquerol, T. Siemieniewska, Pure Appl. Chem. 1985, 57, 603), and/or a mesostructured mesoporous matrix, i.e. having mesopores of uniform size and distributed periodically through said matrix and/or a matrix with hierarchical porosity, i.e. comprising micropores and/or macropores in addition to the mesopores.

The preformed mesoporous matrix can be commercial or synthesized according to the methods known to a person skilled in the art, in particular by use of the "traditional" inorganic synthesis methods: precipitation/gelation from salts under mild temperature and pressure conditions; or "modern" metallo-organic: precipitation/gelation from alkoxides under mild temperature and pressure conditions. In the remainder of the text and for the sake of clarity, these methods are simply called "sol-gel". It is also possible to use "sol-gel" methods combined with the use of specific synthesis processes such as spray-drying, dip-coating, or others.

The preformed mesoporous matrix can be in the form of powder or formed, for example in the form of pelletized, crushed or sieved powder, granules, tablets, beads, wheels, spheres or extrudates (cylinders which can be hollow or not, multilobed cylinders with 2, 3, 4 or 5 lobes for example, twisted cylinders), or rings, etc. Preferentially, a mesoporous matrix is used based on silicon oxide having a specific surface area of 50 to 1200 m$^2$/g, and preferably from 150 m$^2$/g to 1200 m$^2$/g, and a pore volume of at least 0.1 ml/g, and preferably a pore volume comprised between 0.2 and 1.2 ml/g according to the BET method.

The catalyst used according to the invention comprises a content by weight of molybdenum element provided by the precursor of formula (I) and/or (II) and/or (III) according to the invention comprised between 1 and 40%, preferably between 2 and 30%, preferably between 2 and 20%, expressed as a percentage by weight of molybdenum with respect to the weight of the mesoporous matrix.

The catalyst used according to the invention comprises a content by weight of aluminium element provided by the precursor of formulae (IV), (V) and (VI) according to the invention comprised between 0.01 and 50%, preferably between 0.02 and 35%, preferably between 0.02 and 25% expressed as a percentage by weight of aluminium element with respect to the weight of the mesoporous matrix.

The catalyst according to the invention can be prepared according to the methods known to a person skilled in the art.

The deposition of at least one molybdenum-containing precursor and at least one aluminium-containing precursor on the mesoporous matrix can be done before, during or after the forming of the mesoporous matrix.

The deposition of the precursors according to the invention on the mesoporous matrix can be carried out by methods called dry impregnation, impregnation in excess, CVD (chemical vapour deposition), CLD (chemical liquid deposition), etc. described for example in "Catalysis by transition metal sulphides, from molecular theory to industrial application, Eds Hervé Toulhouat and Pascal Raybaud, p137".

For deposition of the precursors according to the invention onto the surface of the preformed mesoporous matrix, the methods called dry impregnation and impregnation in excess are preferred.

Regarding dry impregnation, no particular limitation exists as regards the number of times that said dry impregnation stage is repeated. The different stages can be carried out without solvent or using one or more solvents or mixtures of solvents in which the precursors according to the invention are soluble. These solvents can be polar/protic such as water, methanol or ethanol, polar/aprotic such as toluene or xylene or apolar/aprotic such as hexane. The acidity-basicity of the solutions can also be adapted in order to improve the solubility of the species. Similarly, each of the precursors according to the invention can be impregnated alone or co-impregnated with at least one of the other precursors, the only limitation being the joint presence of at least one molybdenum-containing precursor and of at least one aluminium-containing precursor at the end of the process for the preparation of the catalyst according to the invention.

In a preferred variant, the catalyst can be prepared by dry impregnation according to the process comprising the following stages:

a) solubilization of the molybdenum-containing precursor of formula (I), (II) and/or (III) and the aluminium-containing precursor of formula (IV), (V) and/or (VI) in a volume of solution, preferably aqueous, corresponding to the pore volume of a preformed mesoporous matrix based on oxide, b) impregnation of the preformed mesoporous matrix based on oxide with the solution obtained in stage a), optional maturation of the solid thus obtained, c) optional stage of drying, calcination and/or steam treatment of the solid obtained at the end of stage b), at a pressure greater than or equal to 0.1 MPa or less than or equal to 0.1 MPa, in a temperature range from 50° C. to 1000° C., d) stage of thermal activation of the solid obtained at the end of stage c), at a pressure greater than or equal to 0.1 MPa or less than or equal to 0.1 MPa, in a temperature range from 100° C. to 1000° C.

In another variant, the catalyst can be prepared by dry impregnation according to the process comprising the following stages:

a') solubilization of the molybdenum-containing precursor of formula (I), (II) and/or (III) in a volume of solution, preferably aqueous, corresponding to the pore volume of a preformed mesoporous matrix based on oxide, b') impregnation of the preformed mesoporous matrix based on oxide with the solution obtained in stage a), optional maturation of the solid thus obtained, c') drying stage intended to remove the impregnation solvent from solution a'), d') solubilization of the aluminium-containing precursor of formula (IV), (V) and/or (VI) in a volume of solution, preferably aqueous, corresponding to the pore volume of the solid obtained in stage c'), e') impregnation of the solid obtained in stage c') with the solution obtained in stage d'), optional maturation of the solid thus obtained, f') optional stage of drying, calcination and/or steam treatment of the solid obtained at the end of stage e'), at a pressure greater than or equal to 0.1 MPa or less than or equal to 0.1 MPa, in a temperature range from 50° C. to 1000° C., g') stage of thermal activation of the solid obtained at the end of stage f'), at a pressure greater than or equal to 0.1 MPa or less than or equal to 0.1 MPa, in a temperature range from 100° C. to 1000° C.

Stages a') and d') can be reversed, i.e., the aluminium-containing precursor can be impregnated first then the precursor containing Mo.

The maturation optionally implemented in stages b), b') and e') is carried out in a controlled atmosphere and at a controlled temperature so as to promote the dispersion of said precursor(s) over the entire surface of the preformed mesoporous matrix based on oxide. Advantageously, the maturation is carried out at a temperature comprised between 20 and 120° C. and a pressure comprised between 0.01 and 1 MPa.

Stages c) and/or d) or stages c') and/or f') and/or g') can be carried out under an oxidizing, reducing or neutral atmosphere.

Preferably, optional drying stages c) and f') are carried out in a temperature range from 20° C. to 200° C., preferably from 50° C. to 150° C. and preferably from 100° C. to 130° C. during a period of less than 72 h and preferably less than 24 h.

Preferably, thermal activation stages d) and g') are carried out under a neutral atmosphere at atmospheric pressure in a temperature range from 200° C. to 800° C., preferably from 350° C. to 650° C. Preferably, the neutral atmosphere is nitrogen in a flow rate range from 0.01 to 20 Nl/h per gram of solid obtained at the end of stages c) and f'), preferably from 0.1 to 10 Nl/h per gram of solid obtained at the end of stages c) and f').

In the case of impregnation in excess, the catalyst can be prepared by impregnation in excess according to the process comprising the following stages a") solubilization of the molybdenum-containing precursor of formula (I), (II) and/or (III) and the aluminium-containing precursor of formula (IV), (V) and/or (VI) in a volume of solution, preferably aqueous, corresponding to between 1.5 and 20 times the pore volume of the preformed mesoporous matrix based on oxide, b") impregnation of the preformed mesoporous matrix based on oxide, with the solution obtained in stage a"), filtration and recovery of the solid, optional maturation of the solid thus obtained, c") optional stage of drying, calcination and/or steam treatment of the solid obtained at the end of stage b") at a pressure greater than or equal to 0.1 MPa or less than or equal to 0.1 MPa, in a temperature range from 50° C. to 1000° C., d") stage of thermal activation of the solid obtained at the end of stage c") at a pressure greater than or equal to 0.1 MPa or less than or equal to 0.1 MPa, in a temperature range from 100° C. to 1000° C.

The maturation optionally implemented in stage b") is carried out in a controlled atmosphere and at a controlled temperature so as to promote the dispersion of said precursor over the entire surface of the preformed mesoporous matrix based on oxide. Advantageously, the maturation is carried out at a temperature comprised between 20 and 120° C. and a pressure comprised between 0.01 and 1 MPa.

Preferably, the solubilization of the molybdenum-containing precursor and the aluminium-containing precursor, of formula (I), (II) and/or (III) and of formula (IV), (V) and/or (VI) in stage a") is carried out in a volume of solution corresponding to between 2 and 10 times the pore volume of the preformed mesoporous matrix based on oxide.

Stages c") and/or d") can be carried out under an oxidizing, reducing or neutral atmosphere.

Preferably, optional drying stage c") is carried out in a temperature range from 20° C. to 200° C., preferably from 50° C. to 150° C. and preferably from 100° C. to 130° C. during a period of less than 72 h and preferably less than 24 h.

Preferably, thermal activation stage d") is carried out under a neutral atmosphere at atmospheric pressure in a temperature range from 200° C. to 800° C., preferably from 350° C. to 650° C. Preferably, the neutral atmosphere is nitrogen in a flow rate range from 0.01 to 10 Nl/h per gram of solid obtained at the end of stage c"), preferably from 0.1 to 5 Nl/h per gram of solid obtained at the end of stage c").

Organic compounds, called organic additives, can also be used during the preparation of the catalyst according to the invention. At least one organic additive can be introduced by impregnation onto the mesoporous matrix before the stage of impregnation with the precursors, by co-impregnation with the precursors or post-impregnation after impregnation with the precursors.

The organic compounds or additives used are selected from chelating agents, non-chelating agents, reducing agents and additives known to a person skilled in the art.

Said organic compounds or additives are advantageously selected from mono-, di- or polyalcohols optionally etherified, carboxylic acids (citric acid, acetic acid, etc.), sugars, the non-cyclic mono, di or polysaccharides such as glucose, fructose, maltose, lactose or sucrose, cyclic or non-cyclic esters, cyclic or non-cyclic ethers, ketones, compounds combining several of these functions (ketones, carboxylic acids, ethers, esters, alcohols, amines, etc.), crown ethers, cyclodextrins and compounds containing at least sulphur, or phosphorus or nitrogen such as nitriloacetic acid, ethylenediaminetetraacetic acid, or diethylenetriamine, amino acids and zwitterrionic compounds, used alone or in a mixture.

The impregnation solvent is preferably water but any solvent known to a person skilled in the art can be used.

One or more other metallic elements can also be introduced into the composition of the catalyst used in the process according to the invention. This metallic element can be selected from zinc, nickel, cobalt, tungsten, vanadium, niobium, tantalum, iron and copper. This metallic element is introduced at a content comprised between 0.01 and 10%, and preferably between 0.02 and 5% expressed in % by weight of metal with respect to the weight of the mesoporous matrix based on oxide.

This metallic element can be provided by a compound selected from the salts and/or oxides of zinc, nickel, cobalt, tungsten, vanadium, niobium, tantalum, iron and copper, preferably the salts and/or oxides of zinc, nickel, cobalt, tungsten. Preferably, the compound is a cobalt salt, carboxylate, alkoxide or oxide. Preferably, the compound is $Co(NO_3)_2$ or CoO. Very preferably, the compound is $Co(NO_3)_2$.

This compound can be introduced by impregnation onto the mesoporous matrix before impregnation with the molybdenum-containing precursor of formula (I), (II) and/or (III) and with the aluminium-containing precursor of formula (IV), (V) and/or (VI) by co-impregnation with said precursors or post-impregnation after impregnation with said precursors.

In the case where the catalyst used in the process according to the invention is obtained in the form of powder at the end of the different processes of preparation disclosed above, the latter can be formed according to the methods well known to a person skilled in the art. Thus, it can be in the form of pelletized, crushed or sieved powder, granules, tablets, beads, wheels, spheres or extrudates (cylinders which can be hollow or not, multilobed cylinders with 2, 3, 4 or 5 lobes for example, twisted cylinders), or rings, etc. Preferably, said catalyst is formed as extrudates.

During said forming operation, the catalyst used in the process according to the invention can optionally be mixed with at least one porous oxide material acting as a binder so as to generate the physical properties of the catalyst suitable for the process according to the invention (mechanical strength, attrition resistance etc.).

Said porous oxide material is preferentially a porous oxide material selected from the group formed by alumina, silica, silica-alumina, magnesia, clays, titanium oxide, zirconium oxide, lanthanum oxide, cerium oxide, aluminium phosphates and a mixture of at least two of the oxides mentioned above. Said porous oxide material can also be selected from alumina-boron oxide, alumina-titanium oxide, alumina-zirconia and titanium-zirconium oxide mixtures. The aluminates, for example magnesium, calcium, barium, manganese, iron, cobalt, nickel, copper and zinc aluminates, as well as mixed aluminates, for example those containing at least two of the metals mentioned above, are advantageously used as porous oxide material. Titanates can also be used, for example zinc, nickel, cobalt titanates. Mixtures of alumina and silica and mixtures of alumina with other compounds such as for example the group VIB elements, phosphorus, fluorine or boron can also advantageously be used. It is also possible to use simple, synthetic or natural clays of the dioctahedral phyllosilicate 2:1 type or trioctahedral phyllosilicate 3:1 type such as kaolinite, antigorite, chrysotile, montmorillonite, beidellite, vermiculite, talc, hectorite, saponite, laponite. These clays can optionally be delaminated. Mixtures of alumina and clay and mixtures of silica-alumina and clay can also be advantageously used. Various mixtures using at least two of the compounds mentioned above are also suitable to act as binders.

Optionally, at least one organic adjuvant is also mixed during said forming stage. The presence of said organic adjuvant facilitates forming by extrusion. Said organic adjuvant can advantageously be selected from polyvinylpyrrolidones, cellulose polymers and derivatives thereof, preferably selected from cellulose ethers such as for example Methocel, marketed by the Dow Chemical company, polyvinyl alcohols, polyethylene glycols, polyacrylamides, polysaccharides, natural polymers and derivatives thereof such as for example the alginates, polyesters, polyamides and aromatic polyamides, polyethers, poly(arylether)s, polyurethanes, polysulphones such as polysulphone ethers, heterocyclic polymers, preferably selected from polyimides, polyimide ethers, polyimide esters, polyimide amides, and polybenzimidazoles.

The proportion of said organic adjuvant is advantageously comprised between 0 and 20% by weight, preferably between 0 and 10% by weight and preferably between 0 and 7% by weight, with respect to the total weight of the mesoporous matrix formed.

Metathesis Reaction

The process for the metathesis of olefins carried out by bringing the olefins into contact with the catalyst defined above, is advantageously carried out at a temperature comprised between 0 and 500° C., preferably comprised between 0 and 400° C., more preferably between 20 and 350° C. and yet more preferably between 30 and 350° C.

The metathesis reaction of olefins can be carried out in gas phase or in liquid phase. The reaction can be carried out in batch mode, in a stirred reactor, or in continuous mode, by passing the olefin reagent(s) through a fixed bed, a moving bed or a fluidized bed of catalyst.

The pressure at which the process according to the invention is carried out is not critical. However, for an operation in liquid phase, it is advantageous to maintain a pressure at least equal to the vapour pressure of the reaction mixture at the temperature of the reaction.

The reaction is preferably carried out in the absence of solvents. However, the reaction can be carried out in the presence of a solvent such as a hydrocarbon, or a halogenated, aliphatic, cyclanic or aromatic hydrocarbon.

Olefins capable of reacting by metathesis in the process according to the invention can be linear olefins corresponding to general formula $R^1R^2C=CR^3R^4$, where $R^1$, $R^2$, $R^3$ and $R^4$, identical or different, are hydrogen or a hydrocarbyl radical with 1 to 20 carbon atoms, or olefins with a cyclic structure, the ring comprising from 3 to 20 carbon atoms.

An olefin can either be reacted by itself, or several olefins can be reacted together in a mixture. The process according to the invention is in particular the cross-metathesis reaction of ethylene with 2-butene in order to produce propylene, or the reverse reaction converting propylene to a mixture of ethylene and 2-butene.

Other olefins capable of reacting by metathesis are the monoolefins or polyolefins, linear or cyclic, bearing functional groups such as for example halogen or ester groups. The process can also utilize, in co-metathesis a mixture of the above-mentioned olefins.

In the case of the production of propylene by metathesis between ethylene and 2-butene, the 2-butene can preferably originate from a dimerization reaction of ethylene in the presence of a homogeneous or heterogeneous catalyst known to a person skilled in the art. For example, the 2-butene can originate from a dimerization of ethylene in the presence of a nickel complex of the $NiCl_2(PBu_3)_2$ type producing a mixture of 1-butene and 2-butene by homogeneous catalysis. For example, the 2-butene can originate from a dimerization of ethylene in the presence of a heterogeneous catalyst based on nickel of the $NiSO_4/Al_2O_3$ type producing a mixture of 1-butene and 2-butene by heterogeneous catalysis.

In the case of the production of propylene by metathesis between ethylene and a mixture of 2-butene and 1-butene, a catalyst for the isomerization of 1-butene to 2-butene is preferably used in order to maximize the propylene yield. For example, an oxide catalyst of the MgO or $K_2O$ type can be used to isomerize the 1-butene to 2-butene.

Ethylene can advantageously be obtained by the dehydration of biosourced ethanol by any dehydration method known to a person skilled in the art in order to allow the production of biosourced propylene.

BRIEF DESCRIPTION OF THE DRAWING

The FIGURE represents productivity of catalyst of the Examples

EXAMPLES

In the examples, the molybdenum-containing precursor of the heteropolyanion type $PMo_{12}O_{40}H_3$ and the precursors containing aluminium of the coordination complex type $Al_2(SO_4)_3$ are commercially available.

Example 1A (Not According to the Invention): Preparation of 6.7% Mo/SiO₂ by Dry Impregnation with a Solution of $PMo_{12}O_{40}{}^{3-}.3H^+.30H_2O$ 1.5 g of $PMo_{12}O_{40}{}^{3-}.3H^+.30H_2O$ is dissolved at 60° C. in 11.7 ml of distilled water. On complete dissolution, a silica ($S_{BET}$=462 m²/g, $V_p$=0.75 ml/g) is impregnated with this solution. The solid obtained is matured for 24 h at 25° C. under air. The resulting solid is dried in an oven at 120° C. for 24 h then activated under nitrogen at 550° C. for 2 h.

Example 1B (According to the Invention): Preparation of 6.4% Mo+1% Al/SiO₂ by Dry Impregnation with a Solution of $PMo_{12}O_{40}{}^{3-}.3H^+.30H_2O$ and $Al_2(SO_4)_3.18H_2O$ 1.5 g of $PMo_{12}O_{40}{}^{3-}.3H^+.30H_2O$ and 1.83 g of $Al_2(SO_4)_3.18H_2O$ are dissolved at 60° C. in 11.7 ml of distilled water. On complete dissolution, a silica ($S_{BET}$=462 m²/g, $V_p$=0.75 ml/g) is impregnated with this solution. The solid obtained is matured for 24 h at 25° C. under air. The resulting solid is dried in an oven at 120° C. for 24 h then activated under nitrogen at 550° C. for 2 h.

Example 2: Metathesis of Propylene to Ethylene and 2-Butene 2 g of catalyst prepared in Example 1A and 1B is mixed in a proportion of 50% by weight with silicon carbide (SiC) in a double-jacketed fixed bed reactor. The heat transfer fluid of the double jacket is heated to 70° C. Pure propylene is conveyed to the reactor by means of a Gilson pump and the pressure is set at 4.5 MPa. The productivity of the catalysts expressed in millimole of propylene consumed per gram of catalyst and per hour is quantified as a function of time denoted t (in hours denoted h) in the FIGURE.

The activity of the catalyst 1B according to the invention prepared by impregnation with a molybdenum-containing precursor and an aluminium-containing precursor is greater than the activity of catalyst 1A not according to the invention and prepared by impregnation with a single molybdenum-containing precursor.

The stability of catalyst 1B according to the invention is better than the stability of catalyst 1A not according to the invention.

The invention claimed is:

1. A process for the metathesis of olefins, comprising bringing the olefins into contact with a catalyst comprising a mesoporous matrix and at least the elements molybdenum and aluminium, said elements being incorporated into said matrix using at least two precursors of which at least one precursor contains molybdenum and at least one precursor contains aluminium, in which the catalyst is prepared by dry impregnation according to a process comprising:

a) solubilizing of the molybdenum-containing precursor and the aluminium-containing precursor in a volume of solution corresponding to the pore volume of a preformed mesoporous matrix based on oxide, b) impregnating the preformed mesoporous matrix based on oxide with the solution obtained in a), optionally maturating a solid thus obtained, c) optionally drying, calcining and/or steam treating a solid obtained at the end of b), at a pressure greater than or equal to 0.1 MPa at a temperature of 50° C. to 1000° C., and d) thermally activating a solid obtained at the end of c), at a pressure greater than or equal to 0.1 MPa and a temperature of 100° C. to 1000° C.

2. The process according to claim 1 in which the molybdenum-containing precursor is a coordination complex based on molybdenum and/or polyoxometallate based on molybdenum and/or a (thio)molybdate.

3. The process according to claim 1 in which the molybdenum-containing precursor of the coordination complex type based on molybdenum has formula (I)

$$Mo_m(\!=\!Y)_n(\!\equiv\!N)_{n'}(X)_o(\!=\!CR_2)_r \quad (I)$$

in which, the Y groups, identical to or different from each other, are O, S and or NR', the X groups, identical to or different from each other, are halides, chlorate, bromate, iodate, nitrate, sulphate, hydrogen sulphate, alkylsulphate, thiosulphate, carbonate, hydrogen carbonate, phosphate, hydrogen phosphate, dihydrogen phosphate, substituted or unsubstituted alkyl, cycloalkyl or aryl groups, substituted or unsubstituted cyclopentadienyl groups, alkoxy, aryloxy, siloxy, amide, hydrido, nitro, carboxylate, acetylacetonate, sulphonate, β-diketiminate, iminopyrrolure, amidinate, borate, cyanide, cyanate, thiocyanate or $NR_2$—$CS_2^-$ groups, the R and R' groups, identical to or different from each other, are alkyl, aryl alkoxy or aryloxy groups, m is equal to 1 or 2, n is 0 to 4, n' is 0 to 2, o is 0 to 10, r is 0 to 2, and n+n'+o+r is greater than or equal to 1.

4. The process according to claim 1 in which the molybdenum-containing precursor is a polyoxometallate based on molybdenum of formula (II)

$$(X_xMo_mM_bO_yH_h)^{q-}.nH_2O \quad (II)$$

in which, x is greater than or equal to 0, m is greater than or equal to 2, b is greater than or equal to 0, y is greater than or equal to 7, h is 0 to 12, q is 1 to 20, n is 0 to 200, and x, m, b, y, h, n and q being integers, X being phosphorus, silicon or boron, M being aluminium, zinc, nickel, cobalt, tungsten, vanadium, niobium, tantalum, iron or copper.

5. The process according to claim 4 in which the polyoxometallate is an isopolyanion based on molybdenum in which the subscript x of the element X is equal to 0.

6. The process according to claim 4 in which the polyoxometallate is a heteropolyanion that is a Strandberg heteropolyanion of formula $X_2Mo_5O_{23}H_h{}^{q-}.nH_2O$, an Anderson heteropolyanion of formula $XMo_6O_{24}H_h{}^{q-}.nH_2O$, a Keggin heteropolyanion of formula $XMo_{12}O_{40}H_h{}^{q-}.nH_2O$, a lacunary Keggin heteropolyanion of formula $XMo_{11}O_{39}H_h{}^{-q}.nH_2O$, a lacunary Keggin heteropolyanion of formula $XMo_9O_{34}H_h{}^{q-}.nH_2O$, a Dawson heteropolyanion of formula $X_2Mo_{18}O_{62}H_h{}^{q-}.nH_2O$, or a Preyssler heteropolyanion of formula $X_5Mo_{30}O_{110}H_h{}^{q-}.nH_2O$.

7. The process according to claim 4 in which the polyoxometallate is a heteropolyanion that is a Strandberg heteropolyanion of formula $X_2Mo_4CoO_{23}H_h{}^{q-}.nH_2O$, an Anderson heteropolyanion of formula $XMo_5CoO_{24}H_h{}^{q-}.nH_2O$, a Keggin heteropolyanion of formula $XMo_{11}CoO_{40}H_h{}^{q-}.nH_2O$, a lacunary Keggin heteropolyanion of formula $XMo_{10}CoO_{39}H_h{}^{q-}.nH_2O$, a lacunary Keggin heteropolyanion of formula $XMo_8CoO_{34}H_h{}^{q-}.nH_2O$, a Dawson heteropolyanion of formula $X_2Mo_{17}CoO_{62}H_h{}^{q-}.nH_2O$, or a Preyssler heteropolyanion of formula $X_5Mo_{29}CoO_{110}H_h{}^{q-}.nH_2O$.

8. The process according to claim 1 in which the molybdenum-containing precursor is a (thio)molybdate of formula (III)

$$C_c(MoY_4)_z \qquad (III)$$

in which
C represents an organic or inorganic cation,
the Y groups, identical to or different from each other, are O and or S,
c is 1 to 4, and
z is 1 to 10.

9. The process according to claim 1 in which the aluminium-containing precursor is a coordination complex based on aluminium and/or an aluminium salt and/or a heteropolyanion salt based on aluminium and/or a colloidal solution of alumina.

10. The process according to claim 1 in which the aluminium-containing precursor is a coordination complex based on aluminium of formula (IV)

$$Al_nR_m.xH_2O \qquad (IV)$$

in which,
n is 1 to 3,
m is 1 to 3,
x is 0 to 200, and
the R groups are identical or different from each other, and are hydrogen, a halides, chlorate, bromate, iodate, nitrate, sulphate, hydrogen sulphate, alkylsulphate, thiosulphate, carbonate, hydrogen carbonate, phosphate, hydrogen phosphate, dihydrogen phosphate, a substituted or unsubstituted alkyl, alkenyl, alkynyl, cycloalkyl or aryl group, a substituted or unsubstituted cyclopentadienyl group, or a hydroxy, alkoxy, aryloxy, carboxylate, nitrate, acetylacetonate, sulphonate, or perchlorate group.

11. The process according to claim 1 in which the aluminium-containing precursor is an aluminium salt of formula (V)

$$[Al_nR_m]^-[C]^+.nH_2O \qquad (V)$$

in which,
n is 1 to 3,
m is 1 to 3,
x is 0 to 200,
the R groups are identical to or different from each other, and are hydrogen, an oxo group, a halides, a substituted or unsubstituted alkyl, alkenyl, alkynyl, cycloalkyl or aryl group, a substituted or unsubstituted cyclopentadienyl group, or a hydroxy, alkoxy, aryloxy, carboxylate, sulphonate, nitrate, acetylacetonate, or perchlorate group, and
C is hydrogen, an alkali, an alkaline-earth element, a transition metal, a post-transition metal, a rare earth, or an ammonium or phosphonium cation.

12. The process according to claim 1 in which the aluminium-containing precursor is a heteropolyanion salt based on aluminium of formula (VI)

$$(Al_aM1_mM2_bX_xO_yH_h)^{q-}(C^{r+})_c.nH_2O \qquad (VI)$$

in which,
a is greater than 0,
m is greater than or equal to 1,
b is greater than or equal to 0,
x is greater than or equal to 0,
y is greater than or equal to 10,
h is 0 to 12,
q is 0 to 20,
r is 0 to 20,
c is 0 to 20,
n is 0 to 200,
x, m, y, h, n and q being integers, X being phosphorus, silicon or boron, M1 and M2, identical to or different from each other, being aluminium, zinc, nickel, cobalt, molybdenum, tungsten, vanadium, niobium, tantalum, iron or copper, and
C represents one or more atoms, identical or different, hydrated or non-hydrated, capable of existing in the cationic form, hydrogen, the alkali, alkaline-earth elements, transition metals, post-transition metals and rare earths, in hydrated or non-hydrated forms, selected from the oxygen-containing and/or nitrogen-containing and/or phosphorus-containing organic cations.

13. The process according to claim 1 in which the mesoporous matrix is a matrix based on the oxide of at least one element X that is silicon, titanium, zirconium, magnesium, lanthanum, cerium or mixtures thereof.

14. A process according to claim 1 in which the metathesis reaction is carried out at a temperature of 0 to 500° C.

15. The process according to claim 14 in which the olefins are linear olefins of formula $R^1R^2C\!=\!CR^3R^4$, where $R^1$, $R^2$, $R^3$ and $R^4$, identical or different, are hydrogen or a hydrocarbyl radical of 1 to 20 carbon atoms, or olefins with a cyclic structure, the ring having 3 to 20 carbon atoms.

16. The process according to claim 1 in which the metathesis reaction is the cross-metathesis reaction of ethylene with 2-butene, or the reverse reaction converting propylene to a mixture of ethylene and 2-butene.

17. A process for the metathesis of olefins, comprising bringing the olefins into contact with a catalyst comprising a mesoporous matrix and at least the elements molybdenum and aluminium, said elements being incorporated into said matrix using at least two precursors of which at least one precursor contains molybdenum and at least one precursor contains aluminium, in which the catalyst is prepared by a process comprising the following stages:
a') solubilizing of the molybdenum-containing precursor in a volume of solution corresponding to the pore volume of a preformed mesoporous matrix based on oxide,
b') impregnating of the preformed mesoporous matrix based on oxide with the solution obtained in a), optionally maturing a solid thus obtained,
c') drying to remove impregnation solvent from solution a'), d') solubilizing aluminium-containing precursor in a volume of solution corresponding to the pore volume of solid obtained in c'), e') impregnating a solid obtained in c') with a solution obtained in d'), optionally maturing a solid thus obtained, f') optionally drying, calcining and/or steam treating a solid obtained at the end of stage e'), at a pressure greater than or equal to 0.1 MPa at a temperature of 50° C. to 1000° C., and g') thermally activating a solid obtained at the end of f'), at a pressure greater than or equal to 0.1 MPa, in a temperature of 100° C. to 1000° C.

18. A process for the metathesis of olefins, comprising bringing the olefins into contact with a catalyst comprising a mesoporous matrix and at least the elements molybdenum and aluminium, said elements being incorporated into said matrix using at least two precursors of which at least one precursor contains molybdenum and at least one precursor contains aluminium, in which the catalyst is prepared by impregnation in excess solution according to a process comprising:

a") solubilizing the molybdenum-containing precursor and the aluminium-containing precursor in a volume of solution, corresponding to between 1.5 and 20 times the pore volume of the preformed mesoporous matrix based on oxide, b") impregnating the preformed mesoporous matrix based on oxide, with the solution obtained in a"), filtration and recovery of the solid, optionally maturing of a solid thus obtained, c") optionally drying, calcining and/or steam treating of a solid obtained at the end of b") at a pressure greater than or equal to 0.1 MPa at a temperature of 50° C. to 1000° C., and d") thermally activating of a solid obtained at the end of c") at a pressure greater than or equal to 0.1 MPa at a temperature of 100° C. to 1000° C.

* * * * *